(12) United States Patent
Abdeen Hussan

(10) Patent No.: US 9,110,872 B2
(45) Date of Patent: Aug. 18, 2015

(54) COMPUTER METHOD AND SYSTEM FOR STORING AND PRESENTING SEQUENCE DATA

(75) Inventor: Jagir Razak Jainul Abdeen Hussan, TamilNadu (IN)

(73) Assignee: International Business Machines Corporation, Armonk, NY (US)

( * ) Notice: Subject to any disclaimer, the term of this patent is extended or adjusted under 35 U.S.C. 154(b) by 2591 days.

(21) Appl. No.: 10/699,024

(22) Filed: Oct. 31, 2003

(65) Prior Publication Data
US 2005/0095597 A1 May 5, 2005

(51) Int. Cl.
*G06F 19/00* (2011.01)
*G06F 19/22* (2011.01)
*G06F 19/16* (2011.01)

(52) U.S. Cl.
CPC ............. *G06F 19/22* (2013.01); *G06F 19/16* (2013.01)

(58) Field of Classification Search
None
See application file for complete search history.

(56) References Cited

U.S. PATENT DOCUMENTS 5,832,272 A * 11/1998 Kalantery .................... 717/149

OTHER PUBLICATIONS

Taylor et al., Computer and Chemistry, 1999, vol. 23, p. 365-385.*
Huysmans et al., Proteins: Structure, Function, and Genetics, 1991, vol. 11, p. 59-76.*
Schwartz et al., Genome Research, 2000, vol. 10, p. 577-586.*
Chen et al., Bioinformatics, 2002, vol. 18, No. 12, p. 1696-1698.*
Rigoutsos et al. (Bioinformatics, 1998, vol. 14, No. 1, p. 55-67).*
Orcutt et al. (Nucleic Acids Research, 1982, vol. 10, No. 1, p. 157-174).*
Zhang et al. (Genome Research, 1997, vol. 7, p. 649-656).*
UK CROPNETT (http://ukcrop.net/agr/sequence_display_key#sequence; Published 2001, p. 1-5).*
Martinez et al. (Nucleic Acids Research, 1983, vol. 11, No. 13, p. 4629-4634).*

* cited by examiner

*Primary Examiner* — Pablo S Whaley
(74) *Attorney, Agent, or Firm* — Anthony V.S. England; Manny Schecter

(57) ABSTRACT

Genetic sequence data occurring in genome sequences is represented for efficient access of the sequence information in a defined storage scheme. A described replet-sequence matrix data structure allows the compression and efficient access of sequence information. The data structure allows the dynamic change of ontology: the replet-information table can evolve by adding, updating, removing replets, and the set of replets present in the table represent the ontology at the moment. The data structure enables the sequence information to be processed in parallel, and also enables multiple views of the sequence data to exist along with replet specific information.

19 Claims, 12 Drawing Sheets

Footnote:
2. sequence id 1 in accompanying sequence listing

```
Algorithm reconstruct (sequence-id seq_id)
Begin
        Backbone = getBackbone(seq_id);
            /* getBackbone(seq_id) searches the backbone list and returns the backbone
corresponding to seq_id*/
        Match-Set mr = getheadof(seq_id); /* returns the first match-set instance of the sequence
seq_id*/
        String seq="";
        offset=0;
        Hashtable ht = 0;
        loopcnt=0;bptr=0;
        While(mr!=null){ /* 'null' represents the end of traversal*/
            roffset = getOffset(mr, loopcnt);/* returns the loopcnt^th offset (k+δ) of the
            instance mr*/
            if((roffset – poffset)>0){
               seq=concat(seq, substring(backbone, bptr, roffset-poffset));
               bptr=bptr+roffset-poffset;
            }
            poffset = roffset +length( getreplet(mr) ); /*getreplet(mr) returns the replet in
            mr*/
            seq = concat(seq, resolve(getreplet(mr), getVarInfo(mr,roffset)));
            /*getVarInfor(mr, roffset) provides the variation information for the replete in mr
            at the roffset*/
            /* resolve(replet, var-info) generates the subsequence represented by
            replete+var-info */
            add(mr,ht); /* increments the occurrence count of replete in mr when traversing
            the sequence*/
            loopcnt = no-of-occurance(mr, ht);
            /*no-of-occurance(mr, ht) returns the number of times the replete in mr has
            occurred upto this point of traversal*/
            mr = getnextbasematchset(mr, loopcnt –1);
            /* getnextbasematchset(mr, cnt) provides the next occurring base replets match
            set Instance, this corresponds to the 'cnt^th pointer in the current mr*/
            loopcnt = no-of-occurance (mr, ht);
        }
        seq = concat(seq, substring(backbone, bptr, length(backbone)-1);
        return seq;
End
```

FIG. 7

Backbone = bseq 3: acttgatcggtagctagacggagaagctcccaaaac
Base replets occurring in 3 are {cgcgcgcgcg[1], aaataa..aaa, acagg..ta.gcc..c, tactata.....ttac}
Match-set of the base replets are provided below
1: cgcgcgcgcg[4]
{
Sequence-id = 3
Pattern-id = 1
Array of Matching-offsets <K,δ> = {18,39,83}
Array of Is-base-replet = {true, true, true}
Array of Pointer to Base-replet = {null, null, null}
Array of sequence-formation-edges = {2, 3, 4}
Pointer to next-pattern instance = {...}, Pointer to previous-pattern instance = {...}
}
2: aaataa..aaa
{
Sequence-id = 3
Pattern-id = 2
Array of Matching-offsets <K,δ> = {28}
Array of Is-base-replet = {true}
Array of Pointer to Base-replet = {null}
Array of sequence-formation-edges = {1}
Pointer to next-pattern instance = {...}, Pointer to previous-pattern instance = {...}
}
3: acagg..ta.gcc..c
{
Sequence-id = 3
Pattern-id = 3
Array of Matching-offsets <K,δ> = {49}
Array of Is-base-replet = {true}
Array of Pointer to Base-replet = {null}
Array of sequence-formation-edges = {1}
Pointer to next-pattern instance = {...}, Pointer to previous-pattern instance = {...}
}
4: tactata.....ttac
{
Sequence-id = 3
Pattern-id = 4
Array of Matching-offsets <K,δ> = {93}
Array of Is-base-replet = {true}
Array of Pointer to Base-replet = {null}
Array of sequence-formation-edges = {null}
Pointer to next-pattern instance = {...}, Pointer to previous-pattern instance = {...}
}

Footnote:
4. sequence id 1 in accompanying sequence listing

FIG. 9A

Start of first while loop
    Bptr=0;seq="";offset=0;loopcnt=0;ht={};mr=1
Inside the loop
    Roffset = 18;
Condition true -> Inside 'if'
    Seq = acttgatcggtagctaga[5]
    Bptr= 18
Outside 'if'
    poffset = 28
    seq= acttgatcggtagctagacgcgcgcgcg[6]
    ht={<1,1>}
    loopcnt=1
    mr=2
    loopcnt=0
Start of second loop as mr!=null
    Roffset = 28
Condition false
    Poffset=39
    Seq=acttgatcggtagctagacgcgcgcgcgaaataattaaa[7]
    ht={<1,1>,<2,1>}
    loopcnt=1
    mr=1
    loopcnt=1
Start of third loop as mr!=null
    Roffset =39
Condition false
    Poffset= 49
    Seq= acttgatcggtagctagacgcgcgcgcgaaataattaaacgcgcgcgcg[8]
    ht={<1,2>,<2,1>}
    loopcnt=2
    mr=3
    loopcnt=0
Start of fourth loop as mr!=null
    Roffset = 49
Condition false
    Poffset=65
    Seq= acttgatcggtagctagacgcgcgcgcgaaataattaaacgcgcgcgcgacaggtataggccaac[9]
    ht={<1,2>,<2,1>,<3,1>}
    loopcnt=1
    mr=1
    loopcnt=2

Footnotes:
5. sequence id 2 in accompanying sequence listing
6. sequence id 3 in accompanying sequnece listing
7. sequence id 4 in accompanying sequence listing
8. sequence id 5 in accompanying sequence listing
9. sequence id 6 in accompanying sequence listing

FIG. 9B

Start of fifth loop as mr!=null
    Roffset = 83
Condition true -> Inside 'if'
    Seq=
acttgatcggtagctagacgcgcgcgcgaaataattaaacgcgcgcgcgacaggtataggccaaccggagaagctcccaaaac[10]
    Bptr=36
Outside 'if'
    Poffset=93
    Seq=
acttgatcggtagctagacgcgcgcgcgaaataattaaacgcgcgcgcgacaggtataggccaaccggagaagctcccaaaaccgcgcgcgcg[11]
        ht={<1,3>,<2,1>,<3,1>}
        loopcnt=3
        mr=4
        loopcnt=0

Start of sixth loop as mr!=null
    Roffset =93
Condition false
    Poffset=93
    Seq=
acttgatcggtagctagacgcgcgcgcgaaataattaaacgcgcgcgcgacaggtataggccaaccggagaagctcccaaaaccgcgcgcgcgtactatatcatattac[12]
        ht={<1,3>,<2,1>,<3,1>,<4,1>}
        loopcnt=1
        mr=null
        loopcnt=-1

The while loop is terminated as mr = null;
Outside while loop
    There is no more subsequence of the backbone to be added to 'Seq'
    Return seq Output =
"acttgatcggtagctagacgcgcgcgcgaaataattaaacgcgcgcgcgacaggtataggccaaccggagaagctcccaaaaccgcgcgcgcgtactatatcatattac"[12]

Footnotes:
10. sequence id 7 in accompanying sequence listing
11. sequence id 8 in accompanying sequence listing
12. sequence id 9 in accompanying sequence listing

FIG. 9C

SEQUENCE LISTING

```
<160> NUMBER OF SEQ ID NOS: 18

<210> SEQ ID NO 1
<211> LENGTH: 10
<212> TYPE: DNA
<213> ORGANISM: artificial sequence
<220> FEATURE:
<223> OTHER INFORMATION: chemically synthesized

<400> SEQUENCE: 1
cgcgcgcgcg                                                          10

<210> SEQ ID NO 2
<211> LENGTH: 18
<212> TYPE: DNA
<213> ORGANISM: artificial sequence
<220> FEATURE:
<223> OTHER INFORMATION: chemically synthesized

<400> SEQUENCE: 2
acttgatcgg tagctaga                                                 18

<210> SEQ ID NO 3
<211> LENGTH: 28
<212> TYPE: DNA
<213> ORGANISM: artificial sequence
<220> FEATURE:
<223> OTHER INFORMATION: chemically synthesized

<400> SEQUENCE: 3
acttgatcgg tagctagacg cgcgcgcg                                      28

<210> SEQ ID NO 4
<211> LENGTH: 39
<212> TYPE: DNA
<213> ORGANISM: artificial sequence
<220> FEATURE:
<223> OTHER INFORMATION: chemically synthesized

<400> SEQUENCE: 4
acttgatcgg tagctagacg cgcgcgcgaa ataattaaa                          39

<210> SEQ ID NO 5
<211> LENGTH: 49
<212> TYPE: DNA
<213> ORGANISM: artificial sequence
<220> FEATURE:
<223> OTHER INFORMATION: chemically synthesized

<400> SEQUENCE: 5
acttgatcgg tagctagacg cgcgcgcgaa ataattaaac gcgcgcgcg               49

<210> SEQ ID NO 6
<211> LENGTH: 65
<212> TYPE: DNA
<213> ORGANISM: artificial sequence
<220> FEATURE:
<223> OTHER INFORMATION: chemically synthesized
```

```
<400> SEQUENCE: 6
acttgatcgg tagctagacg cgcgcgcgaa ataattaaac gcgcgcgcga caggtatagg    60
ccaac                                                                65

<210> SEQ ID NO 7
<211> LENGTH: 83
<212> TYPE: DNA
<213> ORGANISM: artificial sequence
<220> FEATURE:
<223> OTHER INFORMATION: chemically synthesized

<400> SEQUENCE: 7
acttgatcgg tagctagacg cgcgcgcgaa ataattaaac gcgcgcgcga caggtatagg    60
ccaaccggag aagctcccaa aac                                           83

<210> SEQ ID NO 8
<211> LENGTH: 93
<212> TYPE: DNA
<213> ORGANISM: artificial sequence
<220> FEATURE:
<223> OTHER INFORMATION: chemically synthesized

<400> SEQUENCE: 8
acttgatcgg tagctagacg cgcgcgcgaa ataattaaac gcgcgcgcga caggtatagg    60
ccaaccggag aagctcccaa aaccgcgcgc gcg                                93

<210> SEQ ID NO 9
<211> LENGTH: 109
<212> TYPE: DNA
<213> ORGANISM: artificial sequence
<220> FEATURE:
<223> OTHER INFORMATION: chemically synthesized

<400> SEQUENCE: 9
acttgatcgg tagctagacg cgcgcgcgaa ataattaaac gcgcgcgcga caggtatagg    60
ccaaccggag aagctcccaa aaccgcgcgc gcgtactata tcatattac               109

<210> SEQ ID NO 10
<211> LENGTH: 96
<212> TYPE: DNA
<213> ORGANISM: artificial sequence
<220> FEATURE:
<223> OTHER INFORMATION: chemically synthesized

<400> SEQUENCE: 10
gctactgggt aatagcagac gcgcgcgcgg agcgcgacca gtgaaataaa aaaacgcgcg    60
cgcgacagga gtaggccttc tactataact gattac                             96

<210> SEQ ID NO 11
<211> LENGTH: 97
<212> TYPE: DNA
<213> ORGANISM: artificial sequence
<220> FEATURE:
<223> OTHER INFORMATION: chemically synthesized

<400> SEQUENCE: 11
cagtaatcgg actccagcgc gcgcgcgaag gagcggtgag gcgaaataat gaaaacaggg    60
ctacgcctgc aaataactaa atactataca ttcttac                            97

<210> SEQ ID NO 12
```

```
<211> LENGTH: 112
<212> TYPE: DNA
<213> ORGANISM: artificial sequence
<220> FEATURE:
<223> OTHER INFORMATION: chemically synthesized

<400> SEQUENCE: 12
caaattgtag gggagcgcgc gcgcgacagg gctacgccaa ccgcgcgcgc gaaataacta      60
aaacctccat actatatatc attaccttac aagacgctta tgcaagggct ac            112

<210> SEQ ID NO 13
<211> LENGTH: 95
<212> TYPE: DNA
<213> ORGANISM: artificial sequence
<220> FEATURE:
<223> OTHER INFORMATION: chemically synthesized

<400> SEQUENCE: 13
cacgggacga aagtaattcg taggggggcgc gcgcgcgaaa taagaaaaac aggcctaagc     60
cttccgcgcg cgcggctatg cggcgaaatc cgagc                               95

<210> SEQ ID NO 14
<211> LENGTH: 33
<212> TYPE: DNA
<213> ORGANISM: artificial sequence
<220> FEATURE:
<223> OTHER INFORMATION: chemically synthesized

<400> SEQUENCE: 14
gctactgggt aatagcagag agcgcgacca gtg                                 33

<210> SEQ ID NO 15
<211> LENGTH: 33
<212> TYPE: DNA
<213> ORGANISM: artificial sequence
<220> FEATURE:
<223> OTHER INFORMATION: chemically synthesized

<400> SEQUENCE: 15
cagtaatcgg actccagaag gagcggtgag gcg                                 33

<210> SEQ ID NO 16
<211> LENGTH: 36
<212> TYPE: DNA
<213> ORGANISM: artificial sequence
<220> FEATURE:
<223> OTHER INFORMATION: chemically synthesized

<400> SEQUENCE: 16
acttgatcgg tagctagacg gagaagctcc caaaac                              36

<210> SEQ ID NO 17
<211> LENGTH: 49
<212> TYPE: DNA
<213> ORGANISM: artificial sequence
<220> FEATURE:
<223> OTHER INFORMATION: chemically synthesized

<400> SEQUENCE: 17
caaattgtag gggagacctc cacttacaag acgcttatgc aagggctac                49

<210> SEQ ID NO 18
<211> LENGTH: 48
<212> TYPE: DNA
<213> ORGANISM: artificial sequence
```

-continued

```
<220> FEATURE:
<223> OTHER INFORMATION: chemically synthesized

<400> SEQUENCE: 18
cacgggacga aagtaattcg tagggggct atgcggcgaa atccgagc          48
```

COMPUTER METHOD AND SYSTEM FOR STORING AND PRESENTING SEQUENCE DATA

FIELD OF THE INVENTION

The present invention relates to multisequence data representation.

BACKGROUND

The sequencing of the human genome has lead to the development of scientific fields such as pharmacogenomics, and personalized medicine. The genetic profile plays a vital role in these fields, which involve a significant amount of processing on the sequence data itself. The complete human genome is thought to be approximately 4 billions bases in length. Thus, storing information for a large population, and allowing efficient access to these sequences, is desirable.

Further, in some cases, treatment provided to a patient for a specific disease depends upon the patient's genetic profile. The genes that are expressed (or not expressed) depend on the genetic profile of the patient. The expression (or non-expression) of some genes leads to the observed disease (phenotypes). The levels of expression and also the kind of expression (which defines the structure of the protein) determine the type of treatment, and the drugs prescribed.

The genetic profile plays a vital role in the drug-discovery process, especially in the initial stages of screening of targets. Companies are expected to develop effective (both in cost and efficacy) drugs, which is possible only by having an effective drug discovery process. The identification and screening of targets and the development/identification of leads takes up a large proportion of the investment in a drug discovery. Every false positive adds a significant cost until identified as ineffective.

Various association studies using genetic profiles and expressed phenotypes allow scientists to prune the target search space effectively. This allows the time taken for discovery to be reduced, and also allows them to choose the target population on whom the drug would be effective and also results in reduced patient targeting time and higher efficacy of the drug on the target population.

Currently, portions of the genetic profile are stored and processing is performed using these short sequences. With new discoveries and ever improving understanding of the genetic sequence, the requirement to store entire sequences becomes inevitable.

The current high-level structures used to annotate sequence data are in the form of markers, exons etc. The bio-dictionary is one such effort, in which markers with sufficient support have been identified and annotated. Similarly, other dictionaries can be developed that contain patterns that identify specific markers/structures among the sequences that are most relevant to the study.

Accordingly, a need exists for an improved manner of data representation for genetic information.

SUMMARY

The techniques described herein represent genetic sequence data as such data occurs in genome sequences. The problem of efficient access of the sequence information is addressed. The described techniques allow users to state their intended use of the sequence information and the usage patterns, which is taken into consideration while defining a storage scheme.

Additional information that is desirably stored with the sequence information is also taken into account. Techniques are described herein for storing the sequence data and, at the same time, allowing efficient access/processing on the data. The techniques described herein are significantly different from the existing compression-based techniques, and requirement specific data storage techniques and leverage the sequence specific characteristics and expected user access model.

The described replet-sequence matrix data structure allows the compression and efficient access of sequence information. The data structure allows the dynamic change of ontology (the replet-information table can evolve by adding, updating, removing replets, and the set of replets present in the table represent the ontology at the moment). The data structure enables the sequence information to be processed in parallel. The data-structure also enables multiple views of the sequence data to exist along with replet specific information.

The variation is stored via an indirection allowing for equivalent sequences to occupy single storage space and hence reduce the amount of storage required. By storing the variations separately, one is able to identify meta-replets among the replets that can be used to perform replet-variation splits, which further reduces storage requirements. Also, experts can identify meta-replets, and variations across that particular replet. Such information is vitally useful for association studies that try to identify such variations and associate them with an observed phenotype(s).

DESCRIPTION OF DRAWINGS

FIG. 7 presents a sequence-reconstruction algorithm to rebuild the original sequence using the techniques described herein

FIGS. 9A to 9C present snapshots of variables for execution of the algorithm of FIG. 7.

DETAILED DESCRIPTION

Figure 1:
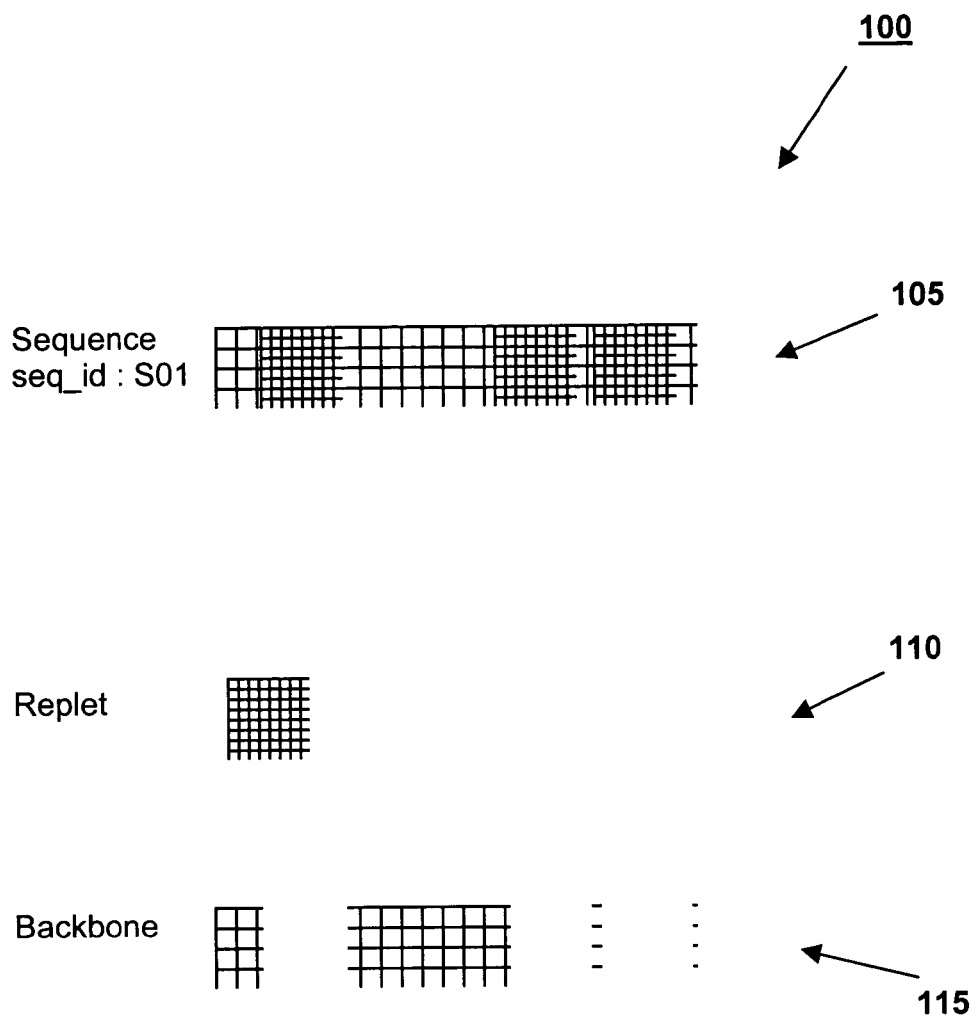
FIG. 1 is a schematic representation of the relation between terms used herein.
Figure 2:
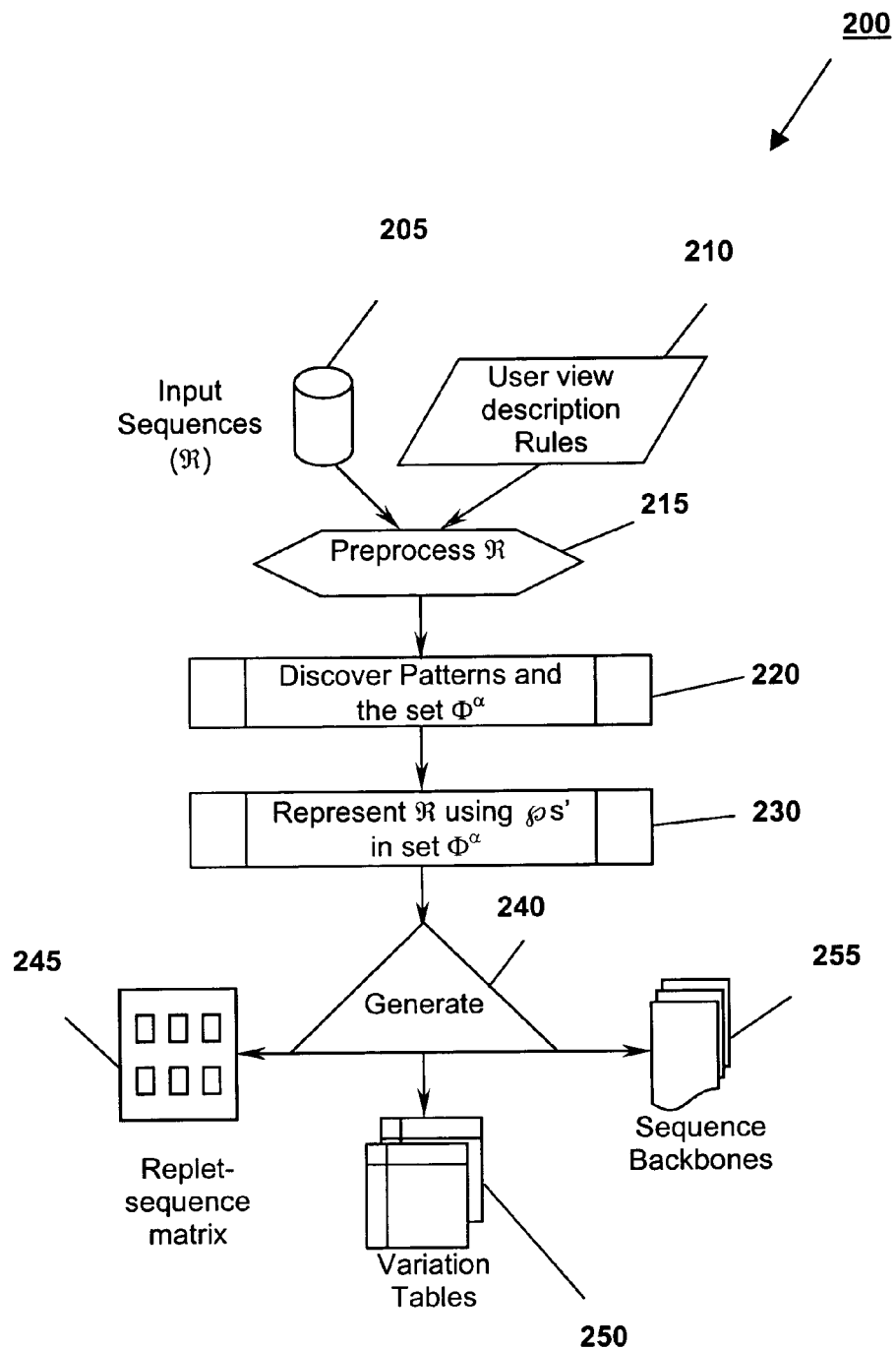
FIG. 2 is a schematic representation, in overview, of the techniques described herein.

Humans are remarkably similar in their genetic makeup. Each individual can be represented by a set of variations that his/her genetic profile has with the consensus genetic sequence of the population to which the person belongs. A great deal of compression is consequently achieved if this observation is used in the storage of genetic sequences of a population. Even though this approach addresses data storage problems associated with storing genetic information, the consensus sequence must be processed for all queries and hence the data processing/accessing capabilities are severely constrained.

The techniques described herein enable efficient storage of a representation for efficient access/processing of the underlying data. Fundamental to data processing is the data and the data structures used. The data structures are based on the view (ontology) that the designer/programmer of the application believes the data implicitly has.

The user's view of the data plays an important role in defining the data-structures used to represent the data and the subsequent methodology of processing the data. In case of sequence data, however, there exists several views and any solution has to take into account accommodating such views by providing physical storage independence of data. The user is able to provide a high level description of his/her view of the data and this description is used to optimize the storage representation to the expected users access pattern.

The high-level view is converted into a set of rules, which allow a subsystem to categorize and preprocess the sequence data in a manner that the input sequences are scrubbed to bring out those characteristics the users is likely to be interested.

The data is preprocessed and different pattern discovery algorithms are run on the data to identify patterns with relatively high support. Different algorithms are performed to eliminate the intrinsic bias an algorithm/algorithmic configuration has towards the patterns identified. Running one or more of these algorithms allows discovering most patterns and eliminates the possibility of missing out significant patterns. These patterns are the high-level structures that are found in the input sequences, and the input sequences can be represented as an ordered set of pattern, variation pairs.

Theoretical Background

The following subsection discusses the theoretical details supporting the techniques described herein. A pattern is comprised of alphabets, let $\Sigma$ denote the set of alphabets in which the sequences are represented. Each character in $\Sigma$ is also called as a residue and the symbol '.' is used as a "don't care" or wildcard character. A pattern $\wp$ is thus a sequence representation of the form ra*r or r+ where $r \in \Sigma$ and $a \in (\Sigma \cup \text{'.'})$. Let $\wp_L$ denote the length of the pattern and $\wp_R$ denote the number of elements from $\Sigma$ contained in $\wp$.

Theorem 1: If there exists a set of sequences $\Re \subseteq \Gamma$, where $\Gamma$ is the space of all sequences of all lengths l, l>0 and $\forall s \in \Gamma$, s belongs to the alphabet $\Sigma$, there exists a non-empty set $\Phi^+$ of patterns such that $\forall \wp \in \Phi^+$, $\wp$ is from the alphabet $\Sigma \cup \text{'.'}$, where '.'represents any alphabet from $\Sigma$.

Proof: The proof for the above theorem is trivial. Since each sequence s belongs to the alphabet $\Sigma$. Each element in $\Sigma$ forms the basis pattern. Each element in $\Sigma$ can be expanded by prefixing and suffixing '.' to any desired length L such that $L \le$ length of (s) and finding a matching subsequence in s for this new pattern and substitute the first and last characters of the matching substring for the first and last characters of the new pattern, thus a valid pattern occurs. The sequence 's' too is a pattern. Thus there exits a non-empty set $\Phi^+$ of patterns.

The ratio of the number of times a pattern $\wp$ occurs in $\Re$ to the number of sequences in $\Re$ is called as support of $\wp$ in $\Re$. Let $f(\wp, y)$ be a metric defined on a $\{\Phi, s \in \Re\}$ space where 'y' is a subsequence of length $\wp$. The metric $f$ provides the amount of information required along with the knowledge of pattern $\wp$ to represent 'y'.

Theorem 2: If $\Phi s$ is the minimum support for a pattern $\wp$ contained in $\Phi$ against $\Re$ (as in Theorem 1), there exists a non-empty set $\Phi^\alpha \subseteq \Phi^+$ of patterns, such that all sequences in $\Re$ are represented as an ordered set $s_j = \{\wp_1, v_1, \wp_2, v_2 \ldots \wp_n, v_n\}$ of pattern, variation pairs ordered based on the position of occurrence on $s_j$, where $v_i$ is the information required along with the $\wp_i$ to represent the subsequence $y_k$ of $s_j$ and $\Sigma f(\wp_{\alpha i}, y_{kj})$ (summation) is minimum ($\Phi^\alpha$ is one among the sets that score the minimum), where 'j' represents the sequence $s_j$ in $\Re$, 'k' the starting position of subsequence y in $s_j$, '$\alpha i$' the $i^{th}$ pattern in set $\Phi^\alpha$.

Proof: Since there exists a set $\Phi$+, there exists subsets $\Phi^-$ of $\Phi$+. There exists a partial ordered relation $\angle$ such that $\Phi^{-\beta} \angle \Phi^{-\alpha}$ if $\Sigma f(\wp_{\beta i}, y_{kj}) < \Sigma f(\wp_{\alpha i}, y_{kj})$ among these $\Phi^-$'s. Order the $\Phi^-$ sets using the above relation and the $\Phi^\alpha$ that has the lowest value is the required $\Phi^\alpha$. Hence there exists a set $\Phi^\alpha$ that represents any $s \in \Re$ such that $\Sigma f(\wp_{\alpha i}, y_{kj})$ is minimum.

The set $\Phi^\alpha$ has an optimal Ds. If all $f$ used for evaluating $\wp$ are linear, the search space for $\Phi^\alpha$ can be pruned by considering only the vertex's of the convex polygon that represents the universe of $\Phi^+$ under the constraints that prune $\Phi$'s with very low information coding/representing content.

Terms and Notation

FIG. 1 schematically represents the relationship between some of the different terms used herein. Definitions for relevant terms are given directly below.

Sequence 105 A sequence is a information theoretic unit (which need not necessarily be only genetic information) composed of finite conceptually related sequences or elements of an alphabet used to represent information. The order of the elements in the sequence determines the relationship between each element or subsequence in the sequence.

Replet 110 The patterns that are used to represent the sequences 105 are called replets 110. These patterns are discovered using existing pattern discovery algorithms.

Backbone 115 There exist some parts of the sequence 105 that do not have any replet match and when all those subsequences that have a replet match are removed, islands of unmatched regions exist. These regions are concatenated whilst maintaining their order of occurrence on the sequence 105. This concatenated sequence is called as the backbone of the respective sequence 105.

Variation Table When a replet is used to represent a subsequence, the characters in the sub-sequence that match against the "don't care" characters in the replet 110 have to be stored along with the replet 110 to reconstruct the subsequence. If matching with mismatches are allowed then the replet 110, the sub-sequence character and offset in the replet has to be stored. The table in which this information is stored is called the variation table.

Match-Set A Match-Set instance describes the positional information of the replet 110 $\wp$ in a sequence 105. A Match-Set is a set of <seq_id, k, $\delta$> ensembles. The variable "seq_id" indicates the sequence 105 where the replet 110 has a match, the sum of "k, $\delta$" provides the starting position of the subsequence (that matches the match-set's replet) in sequence "seq_id". The Match-set data-structure provides an efficient method to create Views on the sequence data. View is composed of an instance of an ontology and each match-set represents a term in the ontology.

Replet-sequence Matrix A collection of Match-Set entries that are related to one another through directed arcs to form a graph as later described. The edges connect the replets that can be used effectively reconstruct the input sequence. This matrix also holds replets 110, which are not necessary to reconstruct the original sequence 105 or any sub sequence.

Base replet-sequence Matrix: The replet-sequence matrix constructed using only those replets 110 that are used to represent a sub-sequence in a sequence 105.

Overview

This subsection describes the techniques and data structures in which the sequences are represented and stored. Distinct components convert high-level description of a user view to set of rules, preprocess the data as per the rules, generate the $\Phi^\alpha$ set (as in Theorem 2), generate/maintain data structures to represent the sequence information and components to access the information in the data structures. The maintenance of sub-sequence specific information is also possible.

The input set of sequences ($\Re$) are processed using the set of replets in $\Phi^\alpha$ and Match-Set data structure generated for each replet $\wp_i$ in $\Phi^\alpha$. A Match-Set data structure is a set of <seq_id, k, $\delta$> ensembles. The variable 'seq_id' indicates the sequence where the pattern has matched, the sum of 'k, $\delta$' provides the starting position of the subsequence (that matches the match-set's replet) in sequence 'seq_id'.

The set $\Phi^\alpha$ can contain maximal, non-maximal replets and replets that intersect and overlap. Thus a subsequence may be matched by more than one replet. The choice among these replets is made in such a way that the final set of replets selected to represent the sequence optimizes a predetermined objective. A procedure for making optimal choices is described below in a subsection entitled "*Identifying optimal patterns*". The set of replets selected does not overlap/intersect, and represents the sequence in an optimal manner.

When a replet is chosen to represent a subsequence of a sequence s, the subsequence is deleted from the sequence s and the variation that is to be stored is obtained. The variation is stored in a list data-structure. If does an entry with an equivalent variation does not exist. Otherwise, the variation is stored as a new entry, and a variation identification var-id is generated to identify the variation.

Each element in the list data-structure has the following structure <var_id,variation>. Each such list data-structure instance is associated with a replet $\wp$, so that all the variations stored in that list data-structure instance correspond to replet $\wp$. There exits a pointer table having the following structure <j,k,var_id> for each replet $\wp$. The variable 'j' represents the sequence in which the replet has one or more match, 'k' the starting position of the subsequence in the sequence (j) to which replet $\wp$ has matched, and 'var_id' is the variation information that is used to recover the subsequence.

The reason for the indirection is that there is large possibility of the variation information to overlap since much of the genetic sequence is similar. Even though each profile is unique, if the profile can be divided into m distinct segments, this uniqueness is due to the variation in one or more of these segments, and is not necessarily due to variation in all segments. Thus storage reduction is achieved by this indirection.

There exist some parts of the sequences that do not have any replet match and when all those sub-sequences that have a replet match, are removed, islands of unmatched regions exist. These regions are concatenated whilst maintaining their order of occurrence on the sequence. This concatenated sequence is called as the backbone of the respective sequence.

Each input sequence is represented using an ordered set of Match-Set entries and a backbone. Each match-set entry represents a subsequence that starts at the location 'k' of the sequence and the variation information can be obtained from the variation table of the replet by using the indirection table for the replet. For these replets the parameter '$\delta$' is zero in the corresponding Match-set entries.

Whenever a subsequence could be represented by one or more replets or one or more combination of replets, a choice is made among them and only one among these is used to represent the subsequence.

The other replets also have an entry in their Match-set entries against the sequences, which enables processing based on these replets. Since the matching subsequence is removed from the sequence, these entries become invalid. The following updates are performed to make these entries valid and enable rebuilding of the subsequence that these replets match. The parameters 'k' and '$\delta$' are adjusted. The parameter 'k' of the Match-Set entry corresponding to replet $\wp$ is set to the 'k' of the replet $\wp_1$ that is chosen to represent the subsequence that replet $\wp$ matches partially or completely. Parameter '$\delta$' is set to the number of positions before ($-\delta$), or after ($+\delta$) 'k' of $\wp_1$ that replet $\wp$ starts matching the subsequence.

Figure 3:
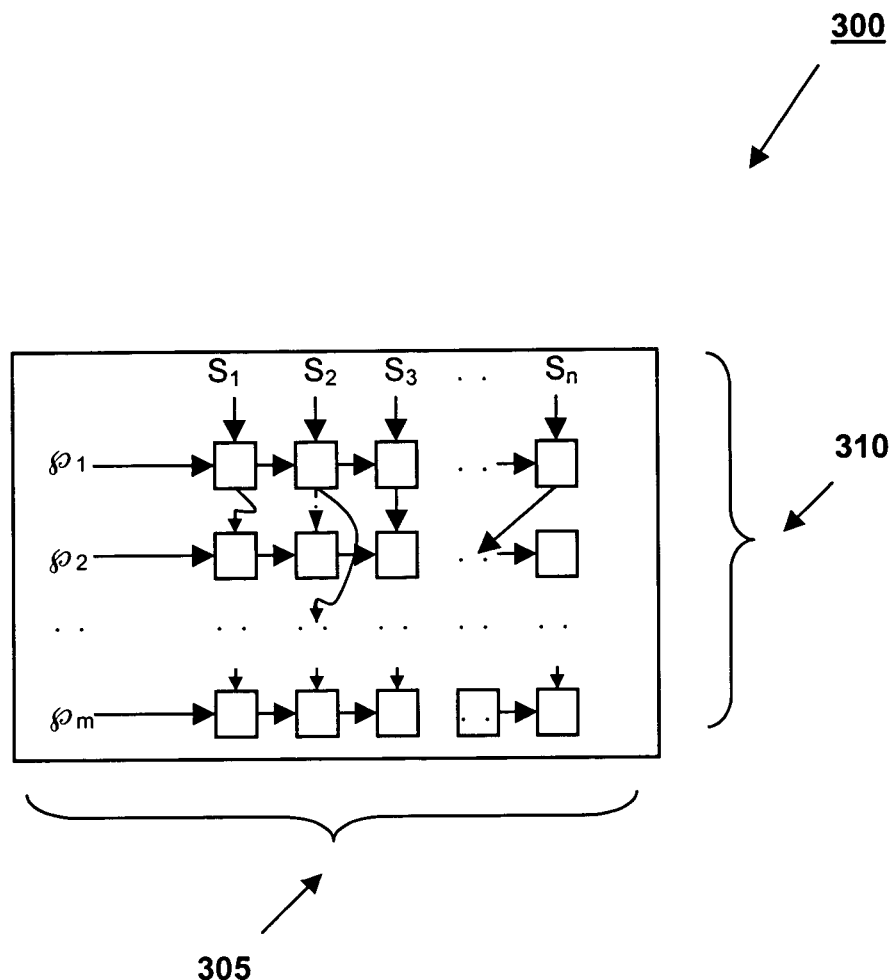
FIG. 3 is a schematic representation of a general replet-sequence matrix.

The parameter '$\delta$' allows such mapping, which is difficult to otherwise perform. Thus the subsequence can be reconstructed using the information in $\wp_1$ and reading this information from the offset '$\delta$'. Thus the Match-Set of all the affected replets are modified to reflect the correct method of access. Connecting the Match-Set entries of all the replets such that the sequence they represent can be traced using pointers among the replets generates a replet-sequence matrix as shown in FIG. 3. FIG. 3 provides a schematic representation of the data structure described herein. Each row of FIG. 3 represents a Match-Set of a replet, and each column represents a sequence that is stored. When the arrows are traversed from the column heading, all the replets matching the sequence are obtained. When the arrows are traversed from the row heading, all the sequences in which the replet has matches are obtained.

The replet-sequence matrix, the variation table and the respective backbones of the sequences with the indirection table completely capture all the information stored in the sequences.

The replets are stored in a replet-information table. Whenever a query string is provided, the query string is matched against the replet-information table. Once the sets of partial/complete matches are obtained, the target strings and the target locus where the query would lie can be obtained. When a sequence is reconstructed, the head pointer $S_j$ for the sequence sj is chosen and the pointer is followed up until the last entry is reached. Each Match-Set entry provides information regarding where the replet starts, what the replet is and, from the variation table, what the variation is. From this information, along with the sequence's backbone, the sequence is built incrementally.

Queries based on the replet-information table and replet-sequence matrix are serviced using any suitable technique. Most processing approaches assume identification of sequences that have some specific traits/patterns, and all such queries are serviced from the information in the replet-information table itself.

If the number of replets is large then secondary replet-information tables can be built with meta-replets that serve to prune the search space in the primary replet-information table for the input queries. Building meta-replets increases the entropy of the system, however, the compression achieved by using the replet-based representation is not diminished by these meta-structures. Use of meta-replets serve to reduce the time complexity of query processing. The increase in space due to these meta-structures is very minimal compared to the large sequence space that the representation represents.

The replet-information table maintains a list of parameters that provide information (on hit count, partial hit count, and so on) that is used to improve the performance as per the current state of processing.

Identifying Optimal Patterns

A description is provided below of a technique for identifying optimal patterns from a given set of patterns and constraints. The identification problem can be generalized as "Given a set of sequences $\Re$, where each sequence belongs to the alphabet $\Sigma$; n sets of patterns $\wp$ have been found using different pattern recognition algorithms on $\Re$. The set $\wp' = \cup \wp_i$ is a set which contains patterns that overlap. If a sequence $s \in \Re$, is represented using $\wp_i$'s". Conflicts arise when there exits more than one $\wp_i$ that can be used to represent a locus in the string s. Decisions have to be made to choose a pattern among the conflicting patterns and the patterns have to be chosen in such a way that the objective ($\Im$) is met. An existing recognition algorithm can be used to discover the different set of $\wp_i$'s from $\Re$.

Also, sometimes the sub-string which a pattern covers might also be partially matched by another pattern, in such cases a decision also has to be made to choose a pattern that should be selected. Deciding on which pattern has to be used on an ad hoc basis may not always lead to a globally optimal solution.

$\Psi(y, \wp)$ is a metric that provides a numerical value representative of the eligibility of the pattern $\wp$ to represent the substring y. A set of patterns can then be determined that are the most eligible to represent sequence s, such that the global penalty/support of using the set of patterns is minimum/maximum.

A technique to identify the optimal set of patterns is described as follows.

Create a directed Graph with all patterns matching a subsequence in the given sequence as nodes connect all the adjacent nodes using edges.

Generate all possible paths containing set of patterns in the order of their matching of the input sequence S, such that no pattern in the path intersects or overlaps any part of the sequence S.

Find the score for each path by summing the $\Psi$'s occurring in the path. If $\Psi$ provides the penalty for choosing the pattern, choose the path with the lowest sum. If $\Psi$ provides support for choosing the pattern, choose the path with the largest sum.

EXAMPLE

Construction of Replet-Sequence-Matrices

An example is now presented of how the data-structure described herein operates. This examples demonstrates how new replets are accommodated, and describes an algorithm and methodology for reconstructing the sequences from the data structures.

Let the set of optimal patterns chosen to represent the set of sequences be $\Phi^\alpha = \{\text{cgcgcgcgcg, aaataa..aaa, acagg..ta.gcc..c, tactata.....ttac}\}$. Let the entire set of patterns chosen for representing the sequences be $\Phi^+$, in which $\Phi^+ = \Phi^\alpha \cup \{\text{aa..a...a}\}$.

Let the new replet to be added after the Replet-sequence matrix for $\Phi^+$ is constructed be {actata}. The example input set of sequences ($\Re$) are represented in Table 1 below.

TABLE 1

```
seq 1:
gctactgggtaatagcagacgcgcgcgcggagcgcgaccagtgaaataaaaaaacgcgcgcgcgacaggagtaggccttct
actataactgattac[1]

seq 2:
cagtaatcggactccagcgcgcgcgcgaaggagcggtgaggcgaaataatgaaaacagggctacgcctgcaaataactaat
actatacattcttac[2]

seq 3:
acttgatcggtagctagacgcgcgcgcgaaataattaaacgcgcgcgcgacaggtataggccaaccggagaagctcccaaa
accgcgcgcgcgtactatatcatattac[3]

seq 4:
caaattgtaggggagcgcgcgcgcgacagggctacgccaaccgcgcgcgcgaaataactaaaacctccatactatatatca
ttaccttacaagacgcttatgcaagggctac[4]

seq 5:
cacgggacgaaagtaattcgtaggggcgcgcgcgcgaaataagaaaaacaggcctaagccttccgcgcgcgcggctatgc
ggcgaaatccgagc[5]
```

Footnotes:
[1]sequence id 9 in accompanying sequence listing
[2]sequence id 10 in accompanying sequence listing
[3]sequence id 11 in accompanying sequence listing
[4]sequence id 12 in accompanying sequence listing
[5]sequence id 13 in accompanying sequence listing The existing pattern discovery algorithm "TEIRESIAS" discovers patterns in multiple sequences that satisfy user-defined criteria such as minimum support, width etc. This algorithm is generally available and is, for example, available in the World Wide Web (www) at cbcsrv(dot)Watson(dot)ibm (dot)com/tspd (dot)html. The TEIRESIAS algorithm is performed for these sequences and the Match-Set entries generated for $\Phi\alpha$ are shown in Table 1 above. The results are presented in Table 2 below, which is a table of Match-Set entries generated by the TEIRESIAS algorithm for the replets.

TABLE 2

| | | | |
|---|---|---|---|
| 10 | 5 | cgcgcgcgcg[6] | 0 19 0 54 1 17 2 18 2 39 2 83 3 15 3 41 4 27 4 64 |
| 5 | 5 | aaataa..aaa | 0 43 1 71 2 28 3 51 4 37 |
| 5 | 5 | acagg..ta.gcc..c | 0 64 1 55 2 49 3 25 4 48 |
| 4 | 4 | tactata.....ttac | 0 80 1 82 2 93 3 69 |

Footnotes:
[6]sequence id 1 in accompanying sequence listing

Table 3 below presents the information obtained by transforming the results in Table 2 above, generated using the TEIRESIAS algorithm, such that the information is structured in accordance with the required Match-Set datastructure. As an example, consider the first entry in Table 2. This entry provides the information concerning the pattern 'cgcgcgcgcg', that is the sequence in which occurs (0) and the offset (19) of the occurrence. The entries of Table 2 are modified to have k,δ parameters, and the resulting set of Match-Set entries as shown in Table 3 below.

TABLE 3

Match-Set as per requirements with k and δ

| Replet | Match-set |
|---|---|
| cgcgcgcgcg[7] | {<0, 19, 0>, <0, 54, 0>, <1, 17, 0>, <2, 18, 0>, <2, 39, 0>, <2, 83, 0>, <3, 15, 0>, <3, 41, 0>, <4, 27, 0>, <4, 64, 0>} |
| aaataa..aaa | {<0, 43, 0>, <1, 71, 0>, <2, 28, 0>, <3, 51, 0>, <4, 37, 0>} |
| acagg..ta.gcc..c | {<0, 64, 0>, <1, 55, 0>, <2, 49, 0>, <3, 25, 0>, <4, 48, 0>} |
| tactata.....ttac | {<0, 80, 0>, <1, 82, 0>, <2, 93, 0>, <3, 69, 0>} |
| aa..a..a | {<0, 43, 0>, <1, 71, 0>, <2, 28, 0>, <3, 51, 0>, <4, 37, 0>} |
| Actata | {<0, 80, 1>, <1, 82, 1>, <2, 93, 1>, <3, 69, 1>} |

Footnotes:
[7]sequence id 1 in accompanying sequence listing

The variation information that has to be stored if patterns $\Phi^\alpha$ are used to represent $\Re$ are listed in Table 4 below.

TABLE 4

Variation Tables

| Replet | Variation Entries |
|---|---|
| cgcgcgcgcg[8] | { } |
| aaataa..aaa | {<0, "aa">, <1, "tg">, <2, "tt">, <3, "ct">, <4, "ga">} |
| acagg..ta.gcc..c | {<0, "aggtt">, <1, "gcctg">, <2, "tagaa">, <3, "gccaa">, <4, "ccatt">} |
| tactata.....ttac | {<0, "actga">, <1, "cattc">, <2, "tcata">, <3, "tatca">} |
| aa..a..a | {<0, "ataaa">, <1, "atatg">, <2, "atact">, <3, "atatt">, <4, "ataga">} |
| Actata | { } |

Footnotes:
[8]sequence id 1 in accompanying sequence listing

The indirection table which provides the mapping between the variation, position, sequence and replet for the $\Phi^\alpha$ replets is provided in Table 5 below.

TABLE 5

Indirection Table

| Replet | Table Entries |
|---|---|
| cgcgcgcgcg[9] | {<0, 19, null>, <0, 54, null>, <1, 17, null>, <2, 18, null>, <2, 39, null>, <2, 83, null>, <3, 15, null>, <3, 41, null>, <4, 27, null>, <4, 64, null>} |
| aaataa..aaa | {<0, 43, 0>, <1, 71, 1>, <2, 28, 2>, <3, 51, 3>, <4, 37, 4>} |
| acagg..ta.gcc..c | {<0, 64, 0>, <1, 55, 1>, <2, 49, 2>, <3, 25, 3>, <4, 48, 4>} |
| tactata.....ttac | {<0, 80, 0>, <1, 82, 2>, <2, 93, 2>, <3, 69, 3>} |
| aa..a..a | {<0, 43, 0>, <1, 71, 1>, <2, 28, 2>, <3, 51, 3>, <4, 37, 4>} |

TABLE 5-continued

Indirection Table

| Replet | Table Entries |
|---|---|
| Actata | {<0, 81, null>, <1, 83, null>, <2, 94, null>, <3, 70, null>} |

Footnotes:
[9]sequence id 1 in accompanying sequence listing

The sequence backbones resulting when $\Phi^\alpha$ replets are used to represent $\Re$ is provided in Table 6 below.

TABLE 6

Sequence backbones bseq 1:
gctactgggtaatagcagagagcgcgaccagtg[10]

bseq 2:
cagtaatcggactccagaaggagcggtgaggcg[11]

bseq 3:
acttgatcggtagctagacggagaagctcccaaaac[12]

bseq 4:
caaattgtaggggagacctccacttacaagacgcttatgcaagggctac[13]

bseq 5:
cacgggacgaaagtaattcgtagggggctatgcggcgaaatccgagc[14]

Figure 4:
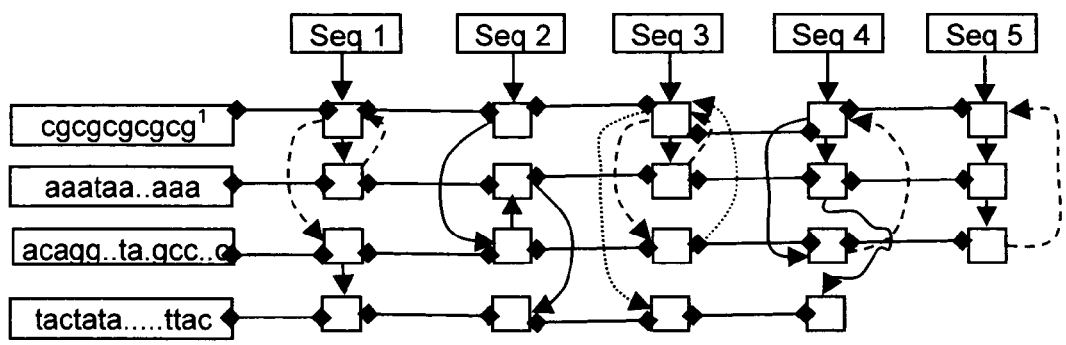
FIG. 4 is a schematic representation of a replet-sequence matrix for elements in $\Phi^\alpha$.
Figure 5:
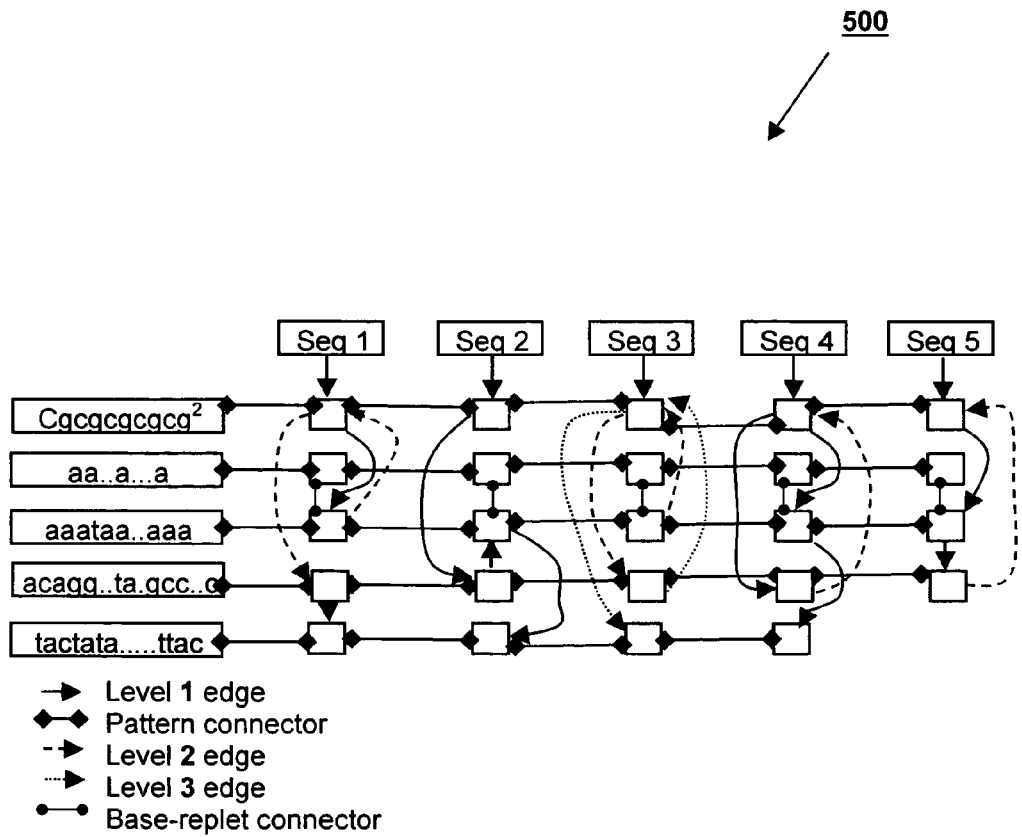
FIG. 5 is a schematic representation of a replet-sequence matrix for elements in $\Phi^+$.
Figure 6:
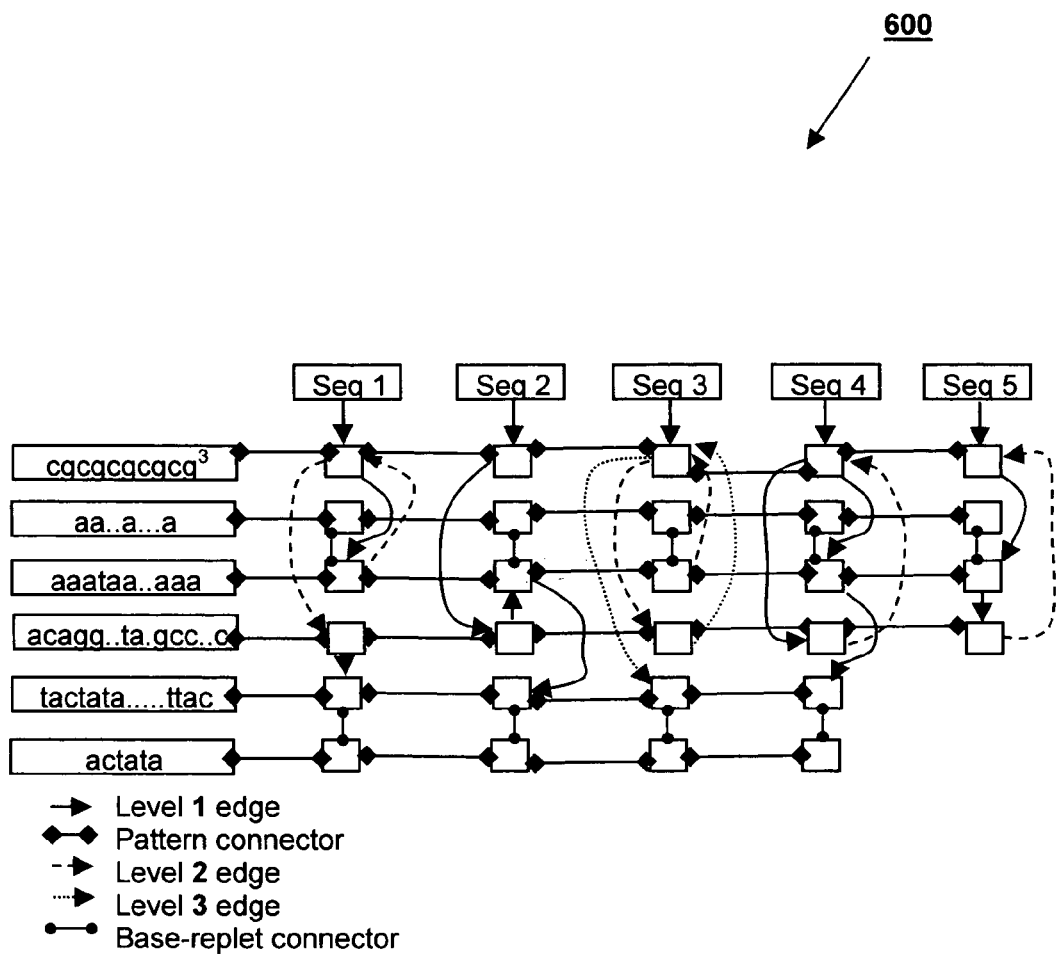
FIG. 6 is a schematic representation of a replet-sequence matrix for elements in $\Phi^+ \cup \{actata\}$.

Footnotes:
[10]sequence id 14 in accompanying sequence listing
[11]sequence id 15 in accompanying sequence listing
[12]sequence id 16 in accompanying sequence listing
[13]sequence id 17 in accompanying sequence listing
[14]sequence id 18 in accompanying sequence listing The Match-Set entries of $\Phi^\alpha$ replets are converted into the Base-replet-sequence matrix, and the schematic representation of the resulting base-replet-sequence-matrix is shown in FIG. 4. Each edge is assigned a level number, when traversing the sequence the next edge to be chosen should always have a higher or equivalent level number to the current edge's level number, when there is more than one edge to choose from.
Base-Replet-Sequence Matrix for Elements in $\Phi^\alpha$ FIG. 5 presents a base-replet-sequence-matrix 500 that is modified to accommodate the overlapping pattern {aa..a...a} and the schematic representation of the resulting replet-sequence-matrix. The base-replet-connector allows the resolving of the base pattern that was chosen against the non-base pattern (In this case, the pattern is {aaataa..aaa}).
Replet-Sequence Matrix for Elements in $\Phi^+$ FIG. 6 presents a replete-sequence-matrix 600 that is modified to include a new replet {actata}. This new replet is a sub-string of the current replet {tactata.....ttac}. Thus base-replet connectors ARE added from actata's replet instances to the corresponding tactata.....ttac's replet instances.
Replet-Sequence Matrix for Elements in $\Phi^+ \cup$ {actata}

Figure 8:
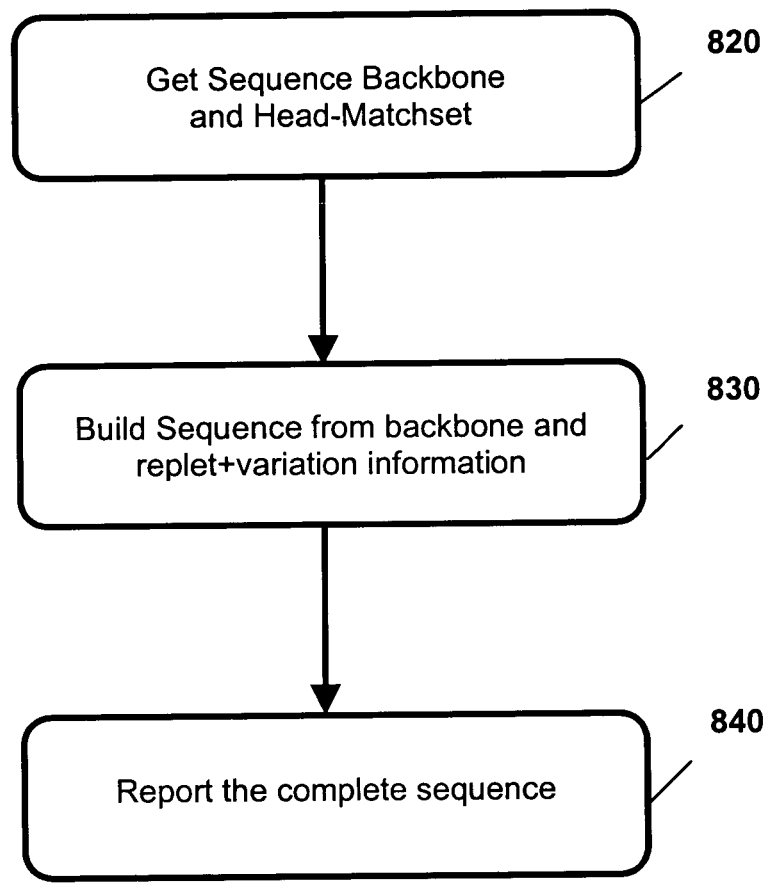
FIG. 8 is a flowchart of steps performed in accordance with the algorithm of FIG. 7.

FIG. 6 presents a replete-sequence-matrix 600 in which the set {actata} is newly added to the structure depicted in FIG. 5.
Pseudo-Code Implementation FIG. 7 presents a pseudo-code algorithm entitled "reconstruct" consisting of three major steps. This sequence-reconstruction algorithm requires the seq_id of the sequence to be reconstructed, the replet-sequence matrix, the variation table, the sequence backbones and the indirection table as input. FIG. 8 is a flowchart which presents key steps of the algorithm in overview.
Step 820—Get Sequence Backbone and Head Obtain the backbone (Backbone) sequence corresponding to sequence (seq_id) to be reconstructed, and also obtain the Match-Set corresponding to the first matching replet. This enables the traversing of all the matching replet's in the order of their matching on the sequence (seq_id). Proceed to step 830.

Step 830—Build Sequence from Backbone and Replete+ Variation Information

Incrementally build the sequence by inserting complete sub-sequences corresponding to the matching replets for the sequence seq_id into the backbone. Resolving the matching replet with the corresponding variation forms the sub-sequences. The variation information is obtained via the indirection table from the variation table. Once the sub-sequence is obtained, the position of this sub-sequence in the sequence (seq_id) is given in the match-set, and using this information the sub-sequence is inserted into the backbone. When this process is completed for the entire list of matching replets, proceed to final step 840.

Step 840—Report the Complete Sequence

At the end of step 840, the complete sequence (seq_id) is reconstructed. Report this sequence as the required sequence.

Reconstructing a Sequence from the Data Structure

The above-described example uses the Replet-sequence-matix generated above and presented in FIGS. 4 to 6. Each match-set entry/replet instance can be represented as the structure presented in Table 7 below.

TABLE 7

Match-Set {
  Sequence-id
  Pattern-id
  Array of Matching-offsets <K,δ>
  Array of Is-base-replet
  Array of Pointer to Base-replet
  Array of sequence-formation-edges
  Pointer to next-pattern instance
  Pointer to previous-pattern instance
}

In Table 7 above, the "Array of sequence-formation-edges" referred to in this table is a vector, such that the entry at index "i" represents the $i^{th}$ instance of the pattern on the sequence "Sequence-id".

The "Array of Matching-offsets" contains the various offsets at which the replet has matched the sequence. The "Array of Is-base-replet" indicates whether the replet was used to represent the sequence at that offset (provided in array of Matching-offsets), or whether something else was used.

FIGS. 9A to 9C present "snapshots" of the variables used in the pseudo-code algorithm presented in FIG. 7 at the various stages in the algorithm when the sequence (seq3) is reconstructed from the data-structure. FIG. 9A is obtained as result of the execution of Step 820 of the algorithm, as described above. FIGS. 9B and 9C depicts the values that each variable in Step 830 takes and the iteration at which those values were obtained. FIG. 9C represents Step 840 of the algorithm, in which the complete rebuilt sequence (seq3) is output as result.

Computer Hardware and Software

Figure 10:
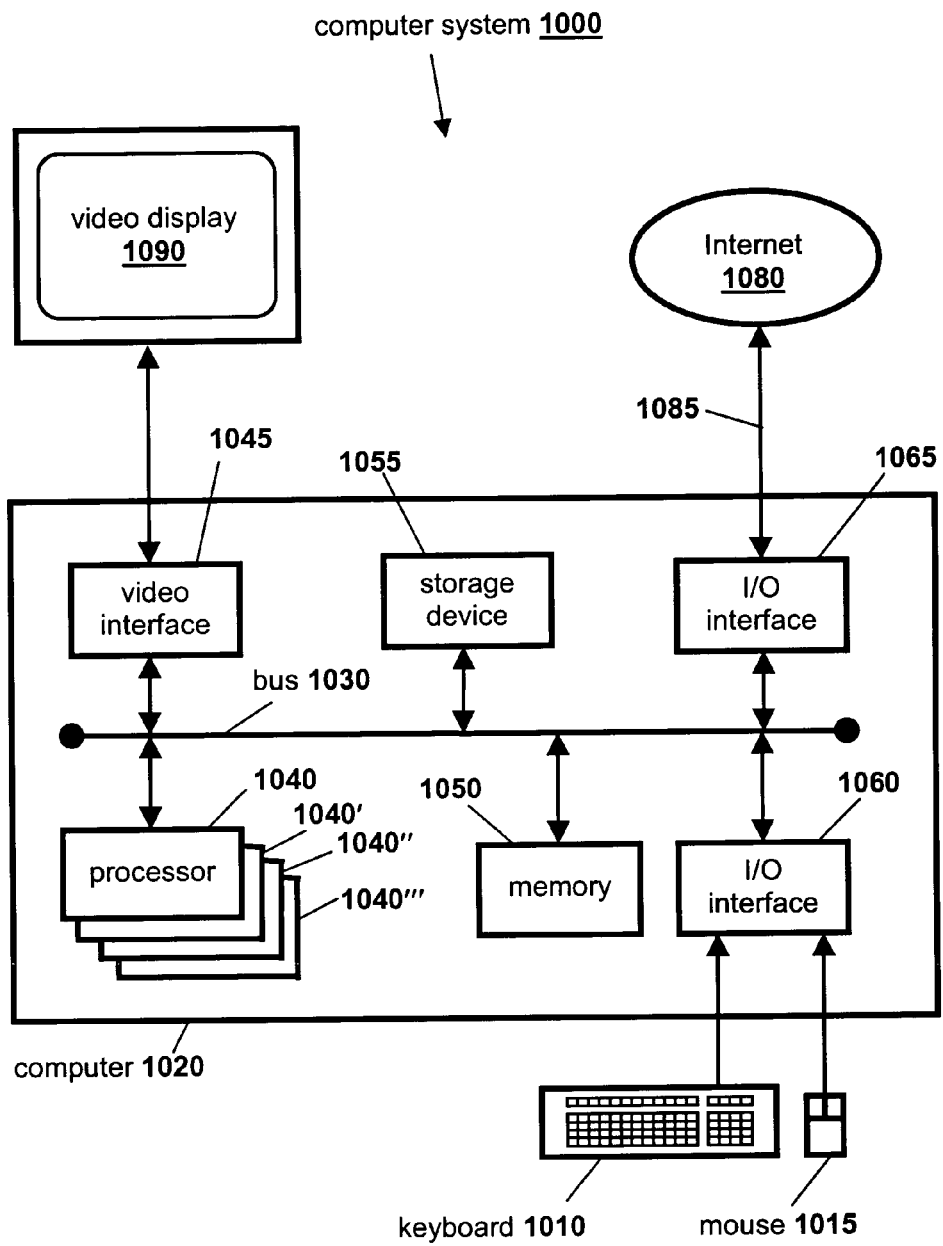
FIG. 10 is a schematic representation of a computer system suitable for performing the techniques described herein.

FIG. 10 is a schematic representation of a computer system 1000 that can be used to implement the data representation techniques described herein. Computer software for performing these techniques executes under a suitable operating system installed on the computer system 1000 to assist in performing the described techniques. This computer software is programmed using any suitable computer programming language, and may be thought of as comprising various software code means for achieving particular steps.

The components of the computer system 1000 include a computer 1020, a keyboard 1010 and mouse 1015, and a video display 1090. The computer 1020 includes a processor 1040, a memory 1050, input/output (I/O) interfaces 1060, 1065, a video interface 1045, and a storage device 1055. Due to the large computational tasks undertaken when performing the techniques described herein, use of a multi-processor system may be desirable. The computer system 1000 may accordingly rely upon multiple processor 1040, 1040" etc as depicted in FIG. 10.

The processor 1040 is a central processing unit (CPU) that executes the operating system and the computer software executing under the operating system. The memory 1050 includes random access memory (RAM) and read-only memory (ROM), and is used under direction of the processor 1040.

The video interface 1045 is connected to video display 1090 and provides video signals for display on the video display 1090. User input to operate the computer 1020 is provided from the keyboard 1010 and mouse 1015. The storage device 1055 can include a disk drive or any other suitable storage medium.

Each of the components of the computer 1020 is connected to an internal bus 1030 that includes data, address, and control buses, to allow components of the computer 1020 to communicate with each other via the bus 1030.

The computer system 1000 can be connected to one or more other similar computers via a input/output (I/O) interface 1065 using a communication channel 1085 to a network, represented as the Internet 1080.

The computer software may be recorded on a portable storage medium, in which case, the computer software program is accessed by the computer system 1000 from the storage device 1055. Alternatively, the computer software can be accessed directly from the Internet 1080 by the computer 1020. In either case, a user can interact with the computer system 1000 using the keyboard 1010 and mouse 1015 to operate the programmed computer software executing on the computer 1020.

Other configurations or types of computer systems can be equally well used to implement the described techniques. The computer system 1000 described above is described only as an example of a particular type of system suitable for implementing the described data representation techniques.

Applications

Performing association studies on the characteristics of the genomic data is a current research endeavor. Most studies try to associate the traits found in one or more regions of the genome with a phenotype (pharmacogenomics) that is very typical of association studies. The users are primarily interested in specific patterns and/or regions of the genome and the associability of these traits to observed phenotypes.

Characteristic to most association based analysis, the performing application is expected to "churn over" the input set of data (sequence) many times. Performing such routines in an ad hoc manner increases the application development time/effort and also brings in other issues of storage/integration of the data.

In "Promoter-specific binding of Rap1 revealed by genome-wide maps of protein-DNA association", Jason D. Lieb et al, *Nature Genetics*, Vol 28, August 2001, the authors' seek to determine the specific characteristics of DNA binding regions, bound by the protein Rap1. In doing so the authors generated all the motifs that resemble the region to which the protein would bind. The study concludes that there exits a molecular mechanism that enables the protein to recognize binding motifs in coding regions than in intergenic regions. Further, the authors studied the significance of Sir proteins with respect to Rap proteins and the role the combination (Rap, Sir) plays in the regulatory logic of the yeast cell.

The authors performed analysis on the genome of the species, and identified several motifs and other patterns of interest during the study. In most cases the findings of are re-utilized in subsequent studies. Typically, the methodology and results of the study are reused but the data generated is not reused due to data representation problems and, at times, the non-reproducibility of the data.

The techniques described herein allow the reuse of data that is generated during a study, and allows the reuse of the data in an efficient and consistent manner. The set of motifs the above-mentioned authors' identified and the role that each motif plays at a specific sequence location is stored as a user view on the base replet-sequence matrix.

This view can be re-utilized in the subsequent studies without requiring the motifs to the re-identified. This reduces the time complexity of the problem under consideration, since the motifs are identified and stored only once. Also since each motif instance can be attributed several properties, the view can be augmented with this information as the study progresses.

There is a growing trend to the publishing of genome-wide maps, and accordingly the number of applications/studies based on such genome-maps is increasing. The representation described herein allows genome-maps to be represented as views, and allows these views to be augmented/modified as the map evolves, without affecting existing applications that use the view. Multiple maps can be represented using multiple views and more views can also be built on these map-views.

In the above-mentioned *Nature Genetics* reference, the authors associated two interacting molecular-mechanisms with an observed phenotype. The regulatory network of some other types of cells or of those involving more than one molecular-mechanism exist and are usual when gene networks of complex organisms such as humans are studied. The time complexity and the number of data-dimensions that the analyzing application processes grows exponentially, and the "turnaround" time for such applications increases unboundedly. Even very small biological systems pose a large computational requirement, making the studies on larger systems is heavily constrained by the computational requirements.

The described representation allows for performing complex analysis even on larger biological systems, wherein multiple data-dimensions (sub-sequence-properties) can be represented and accessed efficiently. If such a representation is not present, then the performing application has to identify motifs (patterns) associate them with the properties and then perform the associations/analysis resulting at runtime. The representation described herein reduces this requirement by multiple orders of magnitude at the cost of space (which is not a significant constraint, as efficient storage facilities are present).

Even though the replet-sequence matrix organization does not attribute any significance with respect to the domain per se. More complex analysis can be performed on the sequence data. The representation also reduces development effort, since the application programmer can assume that these high-level structures exist and proceed with building routines that "churn" on these high-level structures, which is key to developing applications in this field.

Features of the Data Representation Technique

Particular features of the data representation techniques described herein are described in turn below.

Flexibility to Add New Replets

New replets can be introduced, by either splitting existing replets, slicing existing replets etc. New replets need to be introduced whenever the current representation is unable to service queries efficiently sometimes the performance can be greatly improved by performing a complete reorganization of the replet-matrix instance. The representation described herein requires the appropriate modification of the replet-sequence matrix as per the new set of optimal replets and the system easily scales up to the current pattern of access.

Flexibility to Manage Annotations on Sequences

Since each replet's match instance is represented as a <seq_id, k, δ> ensemble, each such ensemble may be annotated with the observed properties via a XML document. This flexibility allows capturing the replet's instance specific properties. The association of an ensemble with an annotation is done via an indirection table, minimizing the number of property document instances to be stored.

Flexibility to Create New Views on the Data

Views can be defined for users, who have different understanding and structuring of the data. For example, a pharmacologist conducting analysis on drug behaviors and their interactions with neuro-transmitters (and hence the related genes/domain sequences), the subsequences that he/she will be interested in are those that are involved directly and remotely with these interactions, hence he/she expects the patterns describing these sequences, build queries and do processing based on the expected patterns.

The view essentially is a replet-variation matrix with a meta-replet table whose replets are formed from the replets in the primary replet-information table. The replet-variation matrix for the view can be easily built on the base replet-sequence matrix. Genome Maps can be easily represented as views and these views can be used for genome-map based processing of the stored sequences.

Flexibility to Perform Processing on Sequence Along with its Identified Properties Views are used to store sequence specific information, such as disease/phenotype markers and hence completely capture all the information regarding the sequences. Subsequently the data can be processed based on these properties and/or sub-sequence structures provided by the view.

Enables Identification of Patterns/Traits Specific to Current Organization/View

The variation tables can also be monitored for the number of variations being stored and if possible the table is split vertically in such a way that effective storage is reduced with no or very less impact on reconstruction time.

The representation is very flexible and agile enough to accommodate changes in the observed replets and methods of access and enables the sequence ontology to evolve with no restriction from storage/access methodology.

CONCLUSION

The requirements for efficient storage and access methods for sequence data are described herein, given the critical role that genetic profiles are expected to play in the area of health care and medicine. These areas not only require the data to be stored efficiently but require the data to be accessed efficiently. Due to the nature of sequence data, multiple views exist and hence multiple structures of data organization exist. Such multiple views are permitted to exist and representational structures that enable efficient storage/access of the data based on these views are possible. These structures are designed to evolve based on the access patterns and the underlying data's organization.

The representational data structures enable physical data independence and hence hide the method of physical storage from the accessing applications. Also the representational structures are architecture independent, even though in the discussion a network/relational view is presented to represent some of the structures, the data-structures can be implemented using other methodologies of organization by suitable representation of the elements in the structures to the target methodology. Further, these structures enable parallel processing of the sequence data, which is key to the target application area since the amount of information to be processed and the complexity is relatively high and parallel processing methods play a vital role in realizing these applications.

Various alterations and modifications can be made to the techniques and arrangements described herein, as would be apparent to one skilled in the relevant art.

I claim:

1. A computer system-implemented method for storing and presenting sequence data, comprising:
   i) specifying a set of replets for analysis by a computer system;
   ii) for each replet in the set, comparing each replet by the computer system to a sequence for determining by the computer system a subsequence of the sequence that matches each replet, if any, wherein the sequence represents a genome sequence;
   iii) generating, by the computer system responsive to the comparing, respective entries of a match-set data structure, the match-set data structure having respective entries for the respective replets, each entry comprising a sequence identification to identify a sequence where a match occurs and offset information to determine a position within the sequence where the matching subsequence of the sequence is located, wherein the offset information comprises a first and second position parameter;
   iv) storing the generated entries of the match-set data structures in a computer readable memory by the computer system;
   v) deleting by the computer system each matching subsequence from the sequence where it is found;
   vi) concatenating by the computer system, in order, unmatched regions of sequences that remain after deleting each matching subsequence to form and store a backbone sequence;
   vii) the computer system generating or receiving a selection of at least a first one of the replets, wherein at least a portion of one of the matching subsequences is matched by a certain plurality of the replets and the received selection includes a selection of at least one of the certain plurality of replets;
   viii) the computer system generating a first instance of the sequence and presenting the first instance of the sequence to a user of the computer system, wherein the generating of the sequence is responsive to the stored backbone sequence and responsive to the at least one of the stored match-set data entries corresponding to the selected at least first one of the replets, wherein the first position parameter of each match-set data structure entry denotes a location in the sequence and the second position parameter of each match-set data structure entry denotes an offset from the location, wherein the selected at least first one of the replets has a position within the sequence, and wherein after receiving the selection the computer system updates the first and second parameters of the entries in the match-set data structure, the updating being responsive to the position of the selected at least first one of the replets;
   ix) the computer system generating or receiving a selection of a second one of the replets; and
   x) the computer system generating and presenting a second instance of the sequence to a user responsive to the at least second one of the replets and wherein the computer system performs the generating of the second instance of the sequence by reference to the updated first and second parameters for the second one of the replets.

2. The method of claim 1, further comprising, before presenting the represented sequence to a user:
   identifying, replets that can be used to represent multiple subsequences.

3. The method of claim 1, further comprising, before presenting the first instance of the sequence to a user:
   segmenting the matching subsequences into multiple parts to account for location-specific variations of the matching subsequences in the sequence data.

4. The method of claim 1, further comprising, before presenting the second instance of the sequence to a user:
   storing replet information in a replet-information table using a pointer, so that equivalent replet sequences occupy single storage space.

5. The method of claim 1, further comprising, before presenting the second instance of the sequence to a user:
   storing multiple views of the sequence data at multiple levels of abstraction.

6. The method of claim 1, wherein storing variations is performed using a pointer.

7. The method of claim 1, wherein, prior to presenting the first instance of the sequence to the user, variations are stored in a list data structure comprising a variation identification.

8. The method of claim 7, wherein the list data structure comprises a subsequence character that matches a "don't care" character in a replet that matches the subsequence.

9. The method of claim 8, wherein, prior to presenting the first instance of the sequence to the user, the position of the subsequence character within the subsequence is stored in the list data structure.

10. The method of claim 7, wherein an indirection pointer points to a variation so that variations common to more than one subsequence are not stored more than once.

11. The method of claim 1, wherein a first instance of the sequence presented to the user is in response to a query by the user.

12. The method of claim 11, wherein a query specifies a replet.

13. The method of claim 1, wherein specifying a set of one or more replets comprises adding a new replet to a pre-existing set for which the steps of claim 1 have been performed.

14. The method of claim 1, wherein specifying a set of one or more replets comprises removing a replet from a pre-existing set for which the steps of claim 1 have been performed.

15. A non-transitory computer readable storage medium having instructions stored thereon for execution by a computer, wherein the instructions, when executed by the computer, cause the computer to implement a method comprising the steps of:

i) specifying a set of replets for analysis by a computer system;

ii) for each replet in the set, comparing each replet by the computer system to a sequence for determining by the computer system a subsequence of the sequence that matches each replet, if any, wherein the sequence represents a genome sequence;

iii) generating, by the computer system responsive to the comparing, respective entries of a match-set data structure, the match-set data structure having respective entries for the respective replets, each entry comprising a sequence identification to identify a subsequence where a match occurs and offset information to determine a position within the sequence where the matching subsequence of the sequence is located, wherein the offset information comprises a first and second position parameter;

iv) storing the generated entries of the match-set data structures in a computer readable memory by the computer system;

v) deleting by the computer system each matching subsequence from the sequence where it is found;

vi) concatenating by the computer system, in order, unmatched regions of sequences that remain after deleting each matching subsequence to form and store a backbone sequence;

vii) the computer system generating or receiving a selection of at least a first one of the replets, wherein at least a portion of one of the matching subsequences is matched by a certain plurality of the replets and the received selection includes a selection of at least one of the certain plurality of replete;

viii) the computer system generating a first instance of the sequence and presenting the first instance of the sequence to a user of the computer system, wherein the generating of the sequence is responsive to the stored backbone sequence and responsive to the at least one of the stored match-set data entries corresponding to the selected at least first one of the replete, wherein the first position parameter of each match-set data structure entry denotes a location in the sequence and the second position parameter of each match-set data structure entry denotes an offset from the location, wherein the selected at least first one of the replets has a position within the sequence, and wherein after receiving the selection the computer system updates the first and second parameters of the entries in the match-set data structure, the selected one of the replets, the updating being responsive to the position of the selected at least first one of the replets;

ix) the computer system generating or receiving a selection of a second one of the replets; and x) the computer system generating and presenting a second instance of the sequence to a user responsive to the at least second one of the replets and wherein the computer system performs the generating of the second instance of the sequence by reference to the updated first and second parameters for the second one of the replets.

16. The computer program product of claim 15, wherein storing variations is performed using a pointer.

17. The computer program product of claim 15, further comprising,
before presenting the first instance of the sequence to a user:
identifying, replets that can be used to represent multiple subsequences.

18. A computer system comprising:
a processor; and
a storage device connected to the processor, wherein the storage device has stored thereon a program for controlling the processor, and wherein the processor is operative with the program to execute the program for performing the steps of:

i) specifying a set of replets for analysis by a computer system;

ii) for each replet in the set, comparing each replet by the computer system to a sequence for determining by the computer system a subsequence of the sequence that matches each replet, if any, wherein the sequence represents a genome sequence;

iii) generating, by the computer system responsive to the comparing, respective entries of a match-set data structure, the match-set data structure having respective entries for the respective replets, each entry comprising a sequence identification to identify a subsequence where a match occurs and offset information to determine a position within the sequence where the matching subsequence of the sequence is located, wherein the offset information comprises a first and second position parameter;

iv) storing the generated entries of the match-set data structures in a computer readable memory by the computer system;

v) deleting by the computer system each matching subsequence from the sequence where it is found;

vi) concatenating by the computer system, in order, unmatched regions of sequences that remain after deleting each matching subsequence to form and store a backbone sequence;

vii) the computer system generating or receiving a selection of at least a first one of the replets, wherein at least a portion of one of the matching subsequences is matched by a certain plurality of the replets and the received selection includes a selection of at least one of the certain plurality of replets;

viii) the computer system generating a first instance of the sequence and presenting the first instance of a the sequence to a user of the computer, wherein the generating of the sequence is responsive to the stored backbone sequence and responsive to the at least one of the stored match-set data entries corresponding to the selected at least first one of the replets, wherein the first position parameter of each match-set data structure entry denotes a location in the sequence and the second position parameter of each match-set data structure entry denotes an offset from the location, wherein the selected at least first one of the replets has a position within the sequence, and wherein after receiving the selection the computer system updates the first and second parameters of the entries in the match-set data structure, the updating being responsive to the position of the selected at least first one of the replets;

ix) the computer system generating or receiving a selection of a second one of the replets; and x) the computer system generating and presenting a second instance of the sequence to a user responsive to the at least second one of the replets and wherein the computer system performs the generating of the second instance of the sequence by reference to the updated first and second parameters for the second one of the replets.

19. The computer system of claim 18, wherein storing variations is performed using a pointer.

* * * * *